(12) United States Patent
Muthiah et al.

(10) Patent No.: US 8,007,884 B2
(45) Date of Patent: Aug. 30, 2011

(54) IRRIGATION, EROSION CONTROL, ROOT GROWTH CONTROL AND CLEAN-UP TECHNIQUES

(75) Inventors: Jeno Muthiah, Bartlett, IL (US); Gerald K. White, Lake Forest, IL (US); Duane R. Rubash, Antioch, IL (US)

(73) Assignee: Synergistic Ventures, Inc., Homer Glen, IL (US)

( * ) Notice: Subject to any disclaimer, the term of this patent is extended or adjusted under 35 U.S.C. 154(b) by 1426 days.

(21) Appl. No.: 10/737,474

(22) Filed: Dec. 16, 2003

(65) Prior Publication Data

US 2004/0133176 A1 Jul. 8, 2004

Related U.S. Application Data

(63) Continuation-in-part of application No. 10/357,907, filed on Feb. 4, 2003, now Pat. No. 7,147,898, which is a continuation-in-part of application No. 09/982,342, filed on Oct. 18, 2001, now abandoned.

(60) Provisional application No. 60/242,926, filed on Oct. 25, 2000.

(51) Int. Cl.
*B32B 1/08* (2006.01)
*B32B 1/02* (2006.01)

(52) U.S. Cl. ............... 428/35.7; 428/34.1; 428/36.9; 428/36.91; 428/143; 604/367; 604/368; 405/15; 405/16; 47/9; 47/56; 47/1.01 F; 47/1.01 T; 47/65.7; 47/65.8; 47/79; 47/80; 47/48.5

(58) Field of Classification Search ............... 428/36.9, 428/36.91, 143, 34.1, 35.7; 604/367, 368; 405/15, 16; 47/9, 56, 1.01 F, 1.01 T, 65.7, 47/65.8, 79, 80, 48.5
See application file for complete search history.

(56) References Cited

U.S. PATENT DOCUMENTS

| | | | | |
|---|---|---|---|---|
| 4,392,908 A | * | 7/1983 | Dehnel | 427/194 |
| 4,418,177 A | * | 11/1983 | Doura et al. | 525/57 |
| 4,710,184 A | * | 12/1987 | Ehret | 604/368 |
| 4,786,550 A | * | 11/1988 | McFarland et al. | 442/118 |
| 4,977,211 A | * | 12/1990 | Doi et al. | 525/54.31 |
| 5,081,791 A | * | 1/1992 | Baron et al. | 47/65.8 |
| 5,419,955 A | | 5/1995 | Ehrhardt et al. | 428/283 |
| 5,720,832 A | | 2/1998 | Minto et al. | 156/62.4 |
| 5,766,522 A | | 6/1998 | Daly et al. | 264/13 |
| 5,817,713 A | * | 10/1998 | Pappas et al. | 524/521 |
| 5,985,434 A | | 11/1999 | Qin et al. | 428/315.5 |
| 6,241,713 B1 | | 6/2001 | Gross et al. | 604/368 |
| 6,358,731 B1 | * | 3/2002 | Hsu | 435/297.5 |
| 6,534,572 B1 | * | 3/2003 | Ahmed et al. | 524/275 |
| 2002/0159727 A1 | * | 10/2002 | Okada et al. | 385/109 |

FOREIGN PATENT DOCUMENTS

FR  2543001 A * 9/1984
WO  WO 90/11181 A1 * 10/1990

OTHER PUBLICATIONS

Material downloaded and printed on Oct. 15, 2001, from www.aquakeep-sap.com website of Atofina.
Frost, Pam and Stone, Dana, *News in Engineering*, The Ohio State University College of Engineering, 3 pages, vol. 70, No. 2, Spring 1998.
Material downloaded and printed on Dec. 11, 2003, from www.hortsorb.com website of Horticultural Alliance, Inc.

* cited by examiner

*Primary Examiner* — Marc Patterson
(74) *Attorney, Agent, or Firm* — Gerald K. White

(57) ABSTRACT

The invention provides processes for coating the surface of substrates such as a sheet, film, foam, fiber, etc., with a curable liquid resin or solution of curable resin, then in one embodiment, stably attaching a superabsorbent polymeric powder to such resin, and then curing the resin to form a coated superabsorbent product. Such substrates may include polymeric materials. Other process embodiments utilizing curable and thermoplastic resinous powders may be used instead of curable liquid resins and resulting products are included in the invention. The coated product may be utilized for water and nutrient retention in combination with irrigation, erosion control, to direct plant root growth, and to clean up standing water and petroleum spills.

25 Claims, No Drawings

IRRIGATION, EROSION CONTROL, ROOT GROWTH CONTROL AND CLEAN-UP TECHNIQUES

This patent application is a continuation-in-part of U.S. patent application Ser. No. 10/357,907 filed Feb. 4, 2003, now U.S. Pat. No. 7,147,898 which in turn is a continuation-in-part of U.S. patent application Ser. No. 09/982,342 filed Oct. 18, 2001 now abandoned. This patent application, through its parent U.S. patent application Ser. No. 09/982,342, claims priority under 35 U.S.C. 119(e) from provisional application Serial No. 60/242,926 filed Oct. 25, 2000 incorporated herein by reference in its entirety.

The present invention relates to highly absorbent products that can, for example, be interposed between liquid permeable and non-liquid permeable sheets to form a disposable absorbent product intended for the absorption of fluids, such as body fluids or used as a wiping sheet and processes of making such products. The invention may also be used as a liquid retention device and element thereof. For example, the invention may be utilized to absorb and retain water and nutrients contained in soil or any other growing media, thereby optimizing plant growth by minimizing loss of water and nutrients, conserving water, and/or reducing the need for future watering. The invention may also be utilized to absorb water and other aqueous media to control erosion of soil and the like, to control and direct plant root growth, and to clean up petroleum spills and standing water.

BACKGROUND OF THE INVENTION

Disposable absorbent products currently find widespread use in many applications. For example, in the infant and childcare areas, diapers and training pants have generally replaced reusable cloth absorbent articles. Other typical disposable absorbent products include feminine care products such as sanitary napkins, panty shields, or tampons; adult incontinence products; and health care products such as surgical drapes or wound dressings. A typical disposable absorbent product generally comprises a composite structure including a top sheet, a back sheet, and an absorbent core structure between the top sheet and back sheet. These products usually include some type of fastening system for fitting the product onto the wearer.

The use of water-swellable, generally water-insoluble absorbent materials, commonly known as superabsorbent polymers ("SAP"), in disposable absorbent personal care products is known. Such absorbent materials are generally employed in absorbent products in order to increase the absorbent capacity of such products while reducing their overall bulk. Such absorbent materials are generally present in absorbent products in the form of small particles in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in water. Clearly, incorporation of such superabsorbent materials in disposable absorbent products can reduce the overall bulk while increasing the absorbent capacity of such products.

The absorbent products mentioned above, such as baby diapers, adult incontinence devices, and feminine hygiene products, may be made with a cellulose fiber fluff-based absorbent core sandwiched between a liquid pervious top sheet, which allows the unobstructed passage of fluid to the absorbent core, and a liquid impervious backing sheet usually of plastic material, which contains the absorbed fluid and prevents it from passing through the absorbent core and soiling the undergarments or clothing of the wearer of the absorbent article.

The absorbent core of these absorbent articles may be constructed of defiberized wood pulp with or without superabsorbent polymer granules. The absorbent core may be formed on a pad-forming unit of a converting machine on a carrier tissue to facilitate processing. Some absorbent core forming units are equipped with layering capability in which a second discrete fluff layer may be laid over a primary fluff-based absorbent layer to form a multi-layer absorbent structure. In these absorbent structures, the primary layer may include loose, superabsorbent polymer granules. It is believed that commercially used superabsorbent polymer granules typically have a coarse size distribution. For example, Atofina reported on its website (www.aquakeep-sap.com) on Oct. 15, 2001, that its AQUAKEEP® superabsorbent polymers may be used in diapers and adult incontinence products and have a particle size distribution of less than 0.5%<45 microns, less than 3%>850 microns; with an average particle size distribution of around 420 microns. Such particle size distribution contains a large amount of particles below 850 microns.

In recent years, market demand for thinner and more comfortable absorbent articles has increased. Ultra-thin feminine napkins are no longer constructed from loose wood pulp, which tends to give a bulky product, but with a roll good-based air-laid absorbent cores in which a roll or coil of pre-formed absorbent core material is unwound directly onto the absorbent pad-making machine without the defiberization step required for fluff-based products. The roll good-based approach results in a product thinness, which cannot be achieved by loose fluff-based technology. As will be seen later, the present invention can produce thinner absorbent products that have the same absorbance properties as thicker products.

U.S. Pat. No. 5,720,832, entitled "Method of Making a Meltblown Nonwoven Web Containing Absorbent Particles", describes yet another approach to the field of the present invention. This patent may contact freshly extruded microfibers with particles that may be composed of superabsorbent materials. The particles are electrostatically charged and applied to the fibers while such fibers are still tacky following extrusion. The result of such application appears to be a physical adherence of the powder to the wet fiber. Adherence can include embedding the particles into the fiber surface when an embossing technique is used.

U.S. Pat. No. 5,419,955 involves the use of superabsorbent particles and sheets to improve absorbency and retention properties. This technique forms a suspension of the particles to avoid problems with powder agglomeration and powder loss.

The invention of this application avoids the need for tacky, freshly extruded fibers as a starting material in a simple, straightforward manner. Typically such freshly extruded fibers are believed to be sufficiently tacky to function as described in aforementioned U.S. Pat. No. 5,720,832 for less than about one minute following extrusion. Thus, a very narrow processing window exists. Fibers or other materials that have been made and stored over a period of time longer than about one minute prior to coating and powder coating may be utilized in this invention. Also, while the need to use particle-containing suspensions is avoided, the objectives of avoiding powder agglomeration and powder loss are achieved by this invention. Accordingly, the objectives of the prior art are achieved without the accompanying constraints.

Superabsorbent polymeric particles, tablets, and emulsions have been used for the purposes of minimizing the loss of water and nutrients in soils, for erosion control, in combination with irrigation procedures, and for clean up of water and petroleum. However, none of these uses appear to involve adhering superabsorbent powders on a substrate or a substrate having openings extending through the substrate. Solid or fibrous polymeric films, such as sheets or strips, or of any other desired shape or form such as round, cylindrical (including wrapped layered cylinders), or any other shapes, constitute a suitable substrate. The above-described uses appear to merely involve the dispersal of superabsorbent polymeric particles in soil and other growing media. Erosion control is believed to employ dispersed particles and/or perforated sheet-like barriers. Neither of these techniques appears to involve the combination of the invention, i.e., adhered superabsorbent polymeric powder stably coated on a substrate.

The long-standing problem in the art of the control of plant root growth has been addressed by using herbicides placed underground to halt root growth into undesired areas such as curbs, sidewalks, roads, paths, septic fields, etc. An example of such technology may be found at the website of Horticulture Alliance, Inc. at http://www.hortsorb.com/Biobarrier.asp. The present invention solves such problem by a different, highly advantageous method, i.e., the roots are attracted to desired areas and therefore growth is minimized in undesired areas. Such method is positive to the plant and its environment when contrasted with the use of herbicides to kill roots at undesired locations when it is considered that herbicides are not placed and thus cannot remain in the ground.

Prior methods of water or petroleum clean up involve placing particles of superabsorbent polymeric powder or petroleum absorbent powder in the area of the standing water or petroleum spill, permitting absorption of water or petroleum, and then collecting the loose particles. On the other hand, the present invention utilizes an element coated with such particles, which may be removed following contact with the water or petroleum. The above-mentioned collection process is thus avoided.

SUMMARY OF THE INVENTION

The process of the present invention involves coating the surface of a polymeric material, such as fiber, sheet, foam, film, etc., with curable liquid resin compositions such as acrylates, unsaturated polyesters, epoxies, urethanes, acrylics, monomer-containing liquids that become superabsorbent when polymerized or cured, etc., applying a superabsorbent polymeric powder to the coating, and then curing the said coating to cause the powder to adhere to the coated polymeric material. It is possible to form a superabsorbent polymer coating by applying monomer-containing liquid resins to the polymeric material surface prior to applying the superabsorbent polymeric powder and then curing the liquid resin particle coating. Curing or polymerizing the monomer will create the desired superabsorbent polymer coating and also adhere the superabsorbent particles thereto. It is also contemplated that a superabsorbent coating, without superabsorbent polymer powders or particles, could be utilized in absorbent materials if so desired. Curing may be effected by thermal or radiation means or a combination thereof. UV curing offers a convenient curing process for said monomer-containing liquid resins.

The present invention also involves a process for stably adhering (or affixing) superabsorbent polymeric powder onto substrates, such as natural or synthetic fibrous materials, polymeric sheets having openings extending through the sheet, etc. One embodiment involves providing a suitable substrate, applying a superabsorbent polymeric powder to a surface of such substrate, further applying a thermoplastic resinous powder to the substrate to form a coating thereon, and then heating the coating to cause at least a portion of the thermoplastic resinous powder to melt and thereby cause the superabsorbent polymeric powder to become stably adhered to the substrate. In addition, the thermoplastic resinous powder may be applied prior to application of the superabsorbent polymeric powder and then stably adhered by heating to cause melting of the thermoplastic resinous powder. Finally, a mixture of superabsorbent polymeric powder and the thermoplastic resinous powder may be applied to the substrate followed by heating to melt the thermoplastic resinous powder to stably adhere the superabsorbent polymeric powder to the underlying substrate.

The present invention also involves a process for stably adhering (or affixing) superabsorbent polymeric powder onto substrates, for example, such as natural or synthetic polymeric fibrous materials or sheets having openings extending through the sheet. One embodiment involves providing a suitable substrate, applying a superabsorbent polymeric powder to a surface of such substrate, further applying a curable resinous powder to the substrate to form a coating thereon, and then heating the coating to cause at least a portion of the curable resinous powder to cure and thereby cause the superabsorbent polymeric powder to become stably adhered to the substrate. In addition, the curable resinous powder may be applied prior to application of the superabsorbent polymeric powder and then stably adhered by heating to cause curing of the curable resinous powder. Finally, a mixture of superabsorbent polymeric powder and the curable resinous powder may be applied to the substrate followed by heating to cure the curable resinous powder to stably adhere the superabsorbent polymeric powder to the underlying substrate.

The present invention also comprises mixtures of superabsorbent polymeric powders and thermoplastic resinous powders for use in the above-discussed processes. Thermoplastic resinous powders including vinyls, polyolefins, nylons, polyesters, and copolymers such as ethylene and vinyl alcohol may be advantageously used in the processes. Such copolymers melt at relatively low temperatures, such as below about 200° C. When the melted thermoplastic resinous powder contacts both the substrate and the superabsorbent polymeric powder, the superabsorbent polymeric powders becomes stably adhered to the substrate.

The present invention also comprises mixtures of superabsorbent polymeric powders and curable resinous powders for use in the above-discussed processes. Commonly available coating powders are suitable. Especially preferred are powders that cure by radiation or thermally at temperatures below about 400° F. As the superabsorbent polymeric powder does not cure, such powder becomes stably adhered to cured resinous powder and thereby ultimately becomes stably adhered to the substrate because upon curing, the curable powder becomes stably adhered to the substrate.

It is also contemplated to provide thin films of thermoplastic resinous materials; to apply superabsorbent polymeric powders to the surface of such films; and to heat the film to cause melting or softening of the film, thereby stably adhering the powders to the film. Alternatively, the superabsorbent polymeric powder may be heated prior to being applied to the film to an extent that the thin film becomes melted or softened at the point of contact between the film and the powder to stably adhere the powder to the thin film.

The present invention also comprises a product having a polymeric material with an at least partially cured resinous coating and further having a superabsorbent polymeric powder adhered to such coating to form a stable, highly absorbent product that can be used for example, as a disposable absorbent product for the absorption of fluids, including body fluids or as a wiping cloth.

As can be appreciated, several long-standing problems in the art are solved by the invention; namely, superabsorbent polymer particle agglomeration and loss; the need for a freshly formed fiber as a starting material (such as the extruded fibers of U.S. Pat. No. 5,720,832); and the need for particle-containing suspensions (such as shown in U.S. Pat. No. 5,419,955). The particles of this invention are located at the surface of the coating rather than mixed within a suspension and thus, effectively disposed to contact and absorb the fluid.

More specifically, the present invention is advantageous over the above discussed prior art because it can stably adhere particles to coated polymeric surfaces. Such result is achieved through use of a liquid resinous coating on the polymeric surface with subsequent curing to adhere the coating to the polymeric material and to the superabsorbent polymeric powder particles. These techniques reduce agglomeration, powder loss, and migration of such powder through the product to the user's skin. Adherence of the particles offers a further advantage due to improved migration of absorbed liquids or fluids from the superabsorbent polymer particles into the coating and polymeric material, thus, the overall absorbency of the absorbent product is enhanced because of stable adherence. Thus, one of the major problems in prior art products is addressed by the present invention through increased migration of such liquids or fluids into other portions of the absorbent product. The invention also requires less bulk than conventional products thereby reducing solid waste disposal space.

The absorbent products of the present invention are suited for use in disposable products including disposable absorbent products such as diapers, diaper liners, training pants, wraps and covers, adult incontinence products, and bed pads; incontinence devices; feminine hygiene products such as sanitary napkins, panty shields, or tampons; other absorbent products such as wipes, bibs, wound dressings and surgical capes or drapes, mattress covers and puddle pads. Accordingly, in another aspect, the present invention relates to a disposable absorbent product utilizing the absorbent products of the present invention as a component.

The above-described liquid retention product also has application to the field of absorbent products. For example, such product could be used alone or in combination with other absorbent materials in previously-described absorbent products such as diapers, feminine hygiene products, adult incontinence products, wiping sheets, surgical drapes, etc. An important aspect of using this product for absorbent product applications is that the size and weight of the absorbent product would be reduced, thereby conferring benefits of comfort and appearance to the user and also creating less solid waste per unit. This latter advantage is an important factor for waste disposal sites. Some absorbent products contain an acquisition layer to absorb and then more slowly disperse urine or other liquid into a superabsorbent polymeric powder containing portion of the absorbent product. In accordance with this invention, the use of fine superabsorbent polymeric powder with its attendant rapid absorption rates may reduce the size of, or eliminate the need for, such acquisition layer.

The process and products of the present invention may also be advantageously employed in the field of water and nutrient retention for incorporation into growing media, such as soil, and in the fields of erosion control, irrigation control, and plant root growth control. A product suitable for such applications comprises water-containing liquid retention devices and elements thereof. Such elements or devices may conveniently comprise sheets (typically polymeric and having holes extending through the sheet), cylinders or other shaped elements and coated, on one or both sides, or at an interior surface, with a superabsorbent polymeric powder and an at least partially melted thermoplastic resinous powder or coated with superabsorbent polymeric powder and an at least partially cured resin.

Specifically, the present invention involves a method of improving water utilization efficiency, comprising placing an element having superabsorbent polymeric powder stably adhered thereto at a desired location under the ground, contacting said superabsorbent polymeric powder with water to cause said water to become absorbed into said superabsorbent polymeric powder, thereby storing said water in said desired location under the ground for future dispersion. This technique is especially desirable for conserving water applied by irrigation processes for agricultural and landscaping purposes. Lesser amounts of water required by future irrigation would be needed because stored water would be consumed following absorption and thus not be permitted to escape through the soil.

In addition, the present invention pertains to a method of directing plant root growth, especially for trees, grass, and any other plants, comprising placing an element having superabsorbent polymeric powder stably adhered thereto at a location under the ground where root growth is desired to be directed, contacting said superabsorbent polymeric powder with water, and optionally also a plant nutrient, to cause said water to become absorbed into said superabsorbent polymeric powder, thereby storing said water and nutrient, if a nutrient is added, in said desired location under the ground to cause plant roots to grow toward said desired location. In addition, a powdered or granular plant nutrient may be stably adhered to the element along with the superabsorbent polymeric powder.

Also, the present invention pertains to a method of reducing soil erosion, comprising placing a barrier element having superabsorbent polymeric powder stably adhered thereto at a desired location under the ground, contacting said superabsorbent polymeric powder with water to cause said water to become absorbed into said superabsorbent polymeric powder, thereby storing said water in said desired location under the ground and thereby reducing soil erosion.

Finally, a method for cleaning up undesired liquids, such as water or petroleum, disposed in an area on a surface is conducted by placing an element having an absorbent material stably adhered thereto in such area to absorb the liquid and then removing the element from the area to result in the removal of at least some of the liquid.

The above-described liquid retention product and absorbent products maybe conveniently formed into coils, cut to length, and placed into a desired product as an absorbent core, thereby affording substantial process advantages. Such advantage is especially important for continuous manufacturing processes.

DETAILED DESCRIPTION OF THE PREFERRED EMBODIMENTS

Polymeric materials may include the superabsorbent polymers set forth below or non-superabsorbent polymers such as polyurethane, polyester, polyethylene, cellulosic, polyolefin, and the like.

It is also contemplated by the invention to utilize co-extruded fibers having a non-superabsorbent polymeric core with a superabsorbent polymeric outer layer as a polymeric material.

Superabsorbent polymeric powders suitable for use in the present invention include, but are not limited to, a wide variety of anionic, cationic, and nonionic materials. Suitable polymers include polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyquaternary ammoniums, natural based polysaccharide polymers such as carboxymethyl celluloses, carboxymethyl starches, hydroxypropyl celluloses, algins, alginates, carrageenans, acrylic grafted starches, acrylic grafted celluloses, chitin, chitosan, and synthetic polypeptides such as polyaspartic acid, polyglutamic acid, polyasparagins, polyglutamines, polylysines, and polyarginines, as well as the salts, copolymers, and mixtures of any of the foregoing polymers. Anionic polyacrylamide polymers are an example of a suitable material.

Curable liquid resins for coating the above-mentioned polymeric materials include acrylates, unsaturated polyesters, epoxies, urethanes, acrylics, monomer-containing liquids that become superabsorbent when polymerized or cured, etc. Because urethanes and superabsorbent polymers absorb moisture, such resins can also contribute to liquid absorption and thus further increase the total absorbency. In this regard, superabsorbent polymers are preferred to urethanes from the standpoint of maximizing the overall liquid absorbency of the absorbent product.

The liquid resins can be applied or coated on the surface of the polymeric material by conventional techniques such as misting, spraying, dipping, curtain coating, slot coating, immersion, aspiration, and the like. Alternatively, the resin may be placed in solution, coated on the polymeric material in liquid solution form, and the solvent then evaporated to leave a highly concentrated coating of the resinous material on the surface of the polymeric material. The balance of the solvent will be evaporated following adherence of the superabsorbent powder particles to the concentrated coating. Polyacrylic acid dissolved in water is a suitable liquid coating. Other combinations of materials and solvents are considered to be part of the invention. Water is a preferred solvent due to environmental factors, but organic solvents such as ethanol and methanol, would also function as a solvent. Evaporation can be achieved by simply sitting at room temperature or accelerated by a temperature increase.

As mentioned above, a liquid-containing monomer may be coated onto the surface of a polymeric material and then cured to form a superabsorbent polymeric coating. While the monomer is in liquid form, superabsorbent powder may be applied to the liquid coating and followed by curing of the liquid by thermal or radiation means. Electrostatic charging of the powder prior to application is optional. Such procedure will cure the liquid monomer-containing resin and stably adhere the powder to the cured coating. In some instances, powder application may not be necessary and reliance can be solely placed on the superabsorbent coating. For example, where the polymeric material is fibrous in nature, a superabsorbent polymer coating without the need for superabsorbent powders could be satisfactory due to the relatively large surface and that a fiber provides as contrasted with a sheet, foam, or film which have lesser surface areas per unit of weight.

Superabsorbent polymeric powders or particles are applied to the liquid resin coated surface of polymeric material through contact. Advantageously, such application can be achieved by directing a stream of superabsorbent polymeric powder particles against the coated polymeric surface. Such streams may be airborne and, if the particle does not readily adhere to the coating, the particles may be electrostatically charged by corona discharge or tribocharging to improve initial adherence prior to at least partially curing said applied coating. Such techniques will serve to improve transfer efficiency of the powder. Another technique is to incorporate additives into the resinous coating composition to improve powder attraction. Surfactants, such as a sodium salt of a sulfonic acid and ammonium salts with long aliphatic chains and the like, are suitable.

Alternatively, a superabsorbent polymeric powder could be applied to a polymeric material surface and then such applied powder can be adhered through the application of a resinous coating and subsequent curing. Said coating may be a liquid resin or a resinous coating powder, which transforms to a solid coating upon curing. Conventional thermosetting or thermoplastic resinous powder coatings are suitable. Curing may be thermal or radiation. The curing temperatures and/or radiation curing procedure will cure the liquid resin or resinous coating powder but the superabsorbent polymeric powders, unlike the resinous liquid or powders, will remain in the same solid particle state because such superabsorbent powders will not melt, flow or otherwise transform during curing. This procedure would serve to contain or adhere the superabsorbent polymeric powder between the polymeric material and coating, thereby achieving the aforesaid advantages of the present invention.

Another embodiment of the process mentioned in the preceding paragraph comprises applying superabsorbent polymeric powders that are coated with a resinous material to a polymeric material and then curing the resinous coating on such powders. Curing results in the cure of the resinous outer coating but does not alter the superabsorbent polymeric powder. Adherence to the polymeric materials is obtained through adhesion of such cured outer coating. Such coated powders could also be contained in a mixture, emulsion, etc.

Another embodiment for adhering superabsorbent polymeric powder to a polymeric material comprises providing a mixture of a superabsorbent polymeric powder and a resinous coating powder, applying such mixture to the polymeric material, and then curing the applied powder mixture to cause adherence to the surface of the polymeric material. Electrostatic charging of the powders prior to application is optional. Curing may be effected by thermal or radiation means. Powder mixing may be performed prior to application, conveniently in a fluidized bed. Mixing may also be performed with use of separate application means (conveniently two or more Corona discharge guns that are so directed toward the surface of the polymeric material) to cause mixing of the respective powders prior to application. Again, the resulting cured product contains superabsorbent polymeric powders contained in a cured resinous coating, which is adhered to the surface of the polymeric material. As above, curing will not alter the state of the superabsorbent polymeric powder.

In any event, once the powder particles are adhered to the coated surface, curing of the coating is effected to further enhance and stabilize the powder coating. Thermal curing through heating to from about 30° to 200° C. for times from about one second to 20 minutes represents typical conditions. Thermal curing can be, for example, achieved in electric, gas fired or induction heated ovens, infrared or microwave heating. Typically, higher temperatures require shorter curing times. Radiation curing can be accomplished by exposure of the coating to ultraviolet, electron beam radiation, etc. Radiation curing, especially by ultraviolet light, is attractive due to its low temperature aspects and consequent lack of potential harm to the polymeric surface. Typically, the coating can be cured using V or D lamps with an illumination dosage of 200 to 600 watts per linear inch discharge. Also a dual cure utilizing thermal and radiation curing is contemplated. Dual curing can be accomplished step-wise or simultaneously. In any event, curing is effective to reduce the tendency of the powder to agglomerate and separate from the coated surface of the polymeric material and also is effective to reduce the loss of fine particles.

Full curing may not be required in that curing to the extent to permit handling and avoid undesirable tackiness is sufficient.

In general, relatively fine particle size distributions are preferred to coarse particle size distributions due to larger surface area and thus, the ability to increase absorbency within normal product usage times. Such increased absorbency reduces the weight of the final product and thus permits a smaller amount of superabsorbent polymer to be used. Such fine particle sizes, within normal produce usage times, in addition to increasing the amount of overall liquid that can be absorbed per unit of superabsorbent polymer, also serve to increase the rate of liquid absorbance. The relatively coarse particle size distribution believed to be used commercially, i.e., having and described in the previously-mentioned website of Atofina, an average particle size of 420 microns, is suitable to achieve certain of the advantages of the invention if attached to the cured coating of the invention. Such certain advantages of the present invention involve stable adherence of the powder to the coated polymeric material, thus minimizing loose powder and powder agglomeration as well as promoting liquid migration throughout the absorbent product. In general, particle size is not essential to attaining such advantage, but as discussed in the next paragraph, particle size distributions less than the coarse commercial powder offer additional advantages.

Smaller particle size distributions can provide other important advantages. First of all, size distributions smaller than the above-discussed coarse size distribution provide increased absorbency rates and, within normal product usage times, provide greater total absorbance. For example, a powder having a large proportion of its particles below about 200 microns exhibits markedly improved absorbance properties when contrasted to a powder having a coarse particle size distribution, such as the above-mentioned Atofina superabsorbent powder. Further benefits may be achieved with particle size distributions wherein a large proportion of the particles are below about 100 microns or even lower.

As can be appreciated, the property relationship that smaller particle size distributions enhance the overall or total amount of liquid that can be absorbed per unit of weight of superabsorbent polymer may enable the absorbent product manufacturer to utilize a smaller amount or weight of superabsorbent polymers and yet achieve the same amount of absorbency achieved by larger particles of the same weight. Such advantage results in the ability to produce smaller, less costly absorbent products that have the same absorbency as that of more bulky products. Another absorbance property of significance is that the smaller the particle size distribution, the higher the rate of liquid absorbance. This property can be utilized advantageously for absorbent products where comfort and hygiene are considered to be important, such as diapers, adult incontinence products, and other absorbent products which absorb body fluids, and the like. Obviously, the combination of improved rate of absorbance coupled with improved total absorbance would especially contribute to the comfort of the user of diapers and adult continence products and be beneficial in the fields of water and nutrient retention and erosion control.

One criteria for selection of a particle size for commercial use is believed to be one of economics; that is, a balance between the cost to achieve a given absorbency benefit vs. the cost savings realized in being able to use a lesser amount of superabsorbent polymer. Thus, cost considerations could result in not using very small sized particles even though the above-mentioned absorbency properties and advantages could be obtained thereby. It is also pointed out that smaller particles, in general, are believed to be more adherent to the liquid resin coating than more coarse particles. On the other hand, very fine particles, such as less than 10 microns, could involve handling and processing problems.

Thermoplastic resinous powders will repeatedly melt when subjected to heat and solidify when cooled.

Thermoplastic resinous powders useful in the invention include vinyls, polyolefins, nylons, polyesters, copolymers of ethylene and vinyl alcohol, and like resinous powders. When heated above their melting points, thermoplastic resins melt and flow to form a coating. When the resin melts and flows, superabsorbent polymeric powders that are proximate to the thermoplastic resinous powders become stably adhered to the coating. Thus, when thermoplastic resinous powders and superabsorbent polymeric powders are coated onto a surface of a substrate, such as a polymeric sheet or fiber, the above-mentioned melting and flow results in particles of superabsorbent polymeric powders becoming stably adhered to the substrate. When heated above the respective melting points, superabsorbent polymeric powders do not melt and flow and thus remain as discrete particles in the coating.

Another process comprises providing a thin film (on the order of about 0.2 mils to about 10 mils) of a thermoplastic resinous material, with or without openings in such films; applying, by suitable means, a superabsorbent polymeric powder to the film; and heating the film to cause melting and thereby stably adhering the superabsorbent polymeric powder to the film. Typical contemplated heating temperatures are on the order of 300° C., higher or lower, depending upon the size of the particles and transfer time of the heated particles to the surface of the film.

Another process embodiment comprises heating the superabsorbent polymeric powder to a sufficient temperature to cause stable adhesion of the superabsorbent polymeric powder to the thermoplastic film. A suitable heating temperature will result in softening of the thermoplastic resinous material. Typical contemplated heating temperatures are on the order of 200° C., higher or lower, depending upon the size of the particles and transfer time of the heated particles to the surface of the film.

When softening is employed, pressure or impingement of the powder onto the film, may be applied to assist adhesion. A convenient method of pressure application comprises a roll assembly. The roll may optionally be heated to further assist adhesion.

Another embodiment comprises heating the superabsorbent polymeric powder, rather than the film, then applying said heated powder to the film to cause melting of the film at the point between the heated powder and the thermoplastic resinous film, thereby stably adhering the powder to the film. Typical contemplated heating temperatures are on the order of 400° C., higher or lower, depending upon the size of the particles and transfer time of the heated particles to the surface of the film.

Another embodiment comprises heating the superabsorbent polymeric powder, rather than the film, then applying said heated powder to the film to cause softening of the film at the point between the heated powder and the thermoplastic resinous film, thereby stably adhering the powder to the film. Typical contemplated heating temperatures are on the order of 300° C., higher or lower, depending upon the size of the particles and transfer time of the heated particles to the surface of the film. Pressure may be subsequently applied to the softened film and superabsorbent polymeric powder to further adhere these materials.

Under either of the above four methods, the film with stably adhered superabsorbent polymeric powder can be used as a core for absorbent products, such as diapers. Obviously, multiple cores may be used should expected liquid input exceed the capacity of a single core.

The melting point of the thermoplastic resin should be lower than that of the substrate to avoid impairing the properties of the substrate. Melting points on the order of about 250° C. are contemplated. Melting points on the order of 200° C. and lower are preferred to avoid such impairment, to reduce processing times, or to reduce energy costs.

It is also desirable, but not essential, that the thermoplastic resin absorb some quantity of water-containing liquids because both the thermoplastic resin and the superabsorbent polymeric powder can then be used to absorb such liquids. Such dual absorbency permits the use of reduced quantities of the superabsorbent polymeric powder, resulting in an overall economy.

For example, a thermoplastic resin that meets both of the above-described properties is a copolymer of ethylene and vinyl alcohol. Typical copolymers include ethylene generally in amounts from about 30 to about 50 mol %. Such copolymers are sold under the trademark EVAL® by Eval Company of America, Pasadena, Tex. The various copolymers are available in a variety of co-polymerization ratios and thus afford a variety of melting points and water absorbency. The choice of a particular copolymer is dependent upon desired processing parameters and product properties.

When applied and coated onto a substrate, separately or as a mixture, the thermoplastic resinous powder and superabsorbent polymeric powder may be present in a variety of amounts. Typically, the amount of thermoplastic resinous powder ranges from 5 wt % to about 20 wt % or higher, balance essentially superabsorbent polymeric powder. Lower amounts of thermoplastic resinous powders are preferred to enhance overall absorbency and thus mixtures containing from about 5 wt % to about 10 wt % thermoplastic resinous powder, balance essentially superabsorbent polymeric powder, are preferred.

Generally, as the particle size decreases for superabsorbent polymeric powders, initial absorbency increases. In the context of this invention, superabsorbent polymeric powder particle size distributions of 100%<210 microns are preferred; and particle size distributions of 100%<90 microns, are more preferable. Superabsorbent polymeric powder particle size distributions having 100%>210 microns lead to the formation of undesirable ball-like discrete particles rather than gel- or paste-like absorption products. The particle size of the thermoplastic resinous powder should be on the order of about 100 microns, with less than 100 microns preferred for liquid absorbency properties. However, when the trade-off between cost of grinding the thermoplastic resinous powder below about 100 microns and the improvement in absorbency is considered, the particle size becomes a matter of choice.

A variety of curable resins including epoxies, saturated and unsaturated polyesters, polyester-epoxy hybrids, acrylics, and admixtures thereof may be utilized in the invention. When heated above their respective curing temperatures or exposed to radiation curing, as the case may be, curable resins flow to form a coating. When the resin cures, superabsorbent polymeric powders that are proximate to the curable resins become stably adhered to the coating. Thus, when curable resin powders and superabsorbent polymeric powders are coated onto a surface of a substrate, such as polymeric sheets or fibers, the above-mentioned curing results in particles of superabsorbent polymeric powders becoming stably adhered to the substrate. When curing occurs, the superabsorbent polymeric powders do not cure or melt and thus remain as discrete particles in the coating.

The curing temperature of the curable resin should be lower than that of the substrate to avoid impairing the properties of such material. Curing temperatures on the order of 400° F. or lower are contemplated, with curing temperatures on the order of 300° F. or lower being preferred to avoid such impairment, to reduce processing times, and to reduce energy costs.

Radiation curable resins include unsaturated polyester resins along with vinyl ether or an acrylate crosslinker and a photoinitiator.

Curable resinous powders that cure at temperatures below about 300° F. and lower are well established. The above-mentioned epoxy, polyester, polyester-hybrid, acrylic, and admixtures thereof resins utilize curing agents and/or catalysts capable of obtaining curing temperatures on the order of 300° F. and less.

Low-temperature curing epoxy resin systems such as set forth in U.S. Pat. Nos. 5,714,206 and 5,721,052, are suitable for use in this invention. Both systems are curable at temperatures of 300° F. or below.

U.S. Pat. No. 5,270,416 also discloses glycidyl methacrylate containing resins crosslinked with carboxylic acid functional crosslinkers and polyesters. If acrylic resins are used, GMA resins such as PD 7690 from Anderson Development Company can be used with DDA as curing agent in presence of catalysts that promote this reaction. Crosslinkers may comprise aliphatic dicarboxylic acid.

U.S. Pat. Nos. 4,147,737 and 5,168,110 disclose other glycidyl functional crosslinkers that can be used with acid functional polyesters as thermosetting powder coating compositions. Epoxy resins such as that are based on bisphenol A can also be used as crosslinkers to form hybrid powder coatings. Such epoxy resins are disclosed in U.S. Pat. No. 5,721,052.

European Patent Application 0 214 448 (A2) discloses compositions containing acid group containing acrylic polymer and epoxy resins.

Acrylic resins for hybrid coating powders are available from SC Johnson. Product designations include SCX820, 831, and 848.

In all of the above compositions, suitable catalysts can be used to enhance low temperature cure characteristics. For all of the thermosetting compositions involving acid functional and glycidyl functional materials suitable catalysts can be chosen from amines (such as DBU), ammonium salts (such as tetra butyl ammonium bromide, benzyl trimethyl ammonium chloride), phosphine (such as triphenyl phosphine), phosphonium salts (such as ethyl triphenyl phosphonium bromide), imidazole (such as 2-methyl imidazole, 2-phenyl imidazole), imidazole adducts (such as P101 from shell, HT 3261 from Ciba Geigy) can be used. U.S. Pat. Nos. 5,169,473 and 4,868,059 disclose catalysts useful for crosslinking glycidyl containing resins. Examples of catalyst that are discussed in these patents are compounds containing amine, phosphine, heterocyclic nitrogen, ammonium, phosphonium, arsonium or sulfonium moieties. Especially preferred are the alkyl-substituted imidazoles; 2,5-chloro-4-ethyl imidazole; and phenyl substituted imidazoles, and mixtures thereof. Even more preferred are 2-methyl imidazole; 2-ethyl, 4-methyl imidazole; 1,2-dimethylimidazole; and 2-phenyl imidazole. Especially preferred is 2-methyl imidazole. Particularly suitable catalysts are those quaternary phosphonium and ammonium compounds such as, for example, ethyltriphenylphosphonium chloride, ethyltriphenylphosphonium bromide, ethyltriphenylphosphonium iodide, ethyltriphenylphosphonium acetate, ethyltriphenylphosphonium diacetate (ethyltriphenylphosphonium acetate acetic acid complex), ethyltriphenylphosphonium tetrahaloborate, tetrabutylphosphonium chloride, tetrabutylphosphonium bromide, tetrabutylphosphonium iodide, tetrabutylphosphonium acetate, tetrabutylphosphonium diacetate (tetrabutylphosphonium acetate acetic acid complex), tetrabutylphosphonium tetrahaloborate, butyltriphenylphosphonium tetrabromobisphenate, butyltriphenylphosphonium bisphenate, butyltriphenylphosphonium bicarbonate, benzyltrimethylammonium chloride, benzyltrimethylammonium hydroxide, benzyltrimethylammonium tetrahaloborate, tetramethylammonium hydroxide, tetrabutylammonium hydroxide, tetrabutylammonium tetrahaloborate, and mixtures thereof and the like.

Other suitable catalysts include tertiary amines such as, for example, triethylamine, tripropylamine, tributylamine, benzyldimethylamine, imidazoles such as 2-methylimidazole mixtures thereof and the like.

Other suitable catalysts include ammonium compounds such as, for example, triethylamine.HCl complex, triethylamine.HBr complex, triethylamine.HI complex, triethylamine.tetrahaloboric acid complex, tributylamine.HCl complex, tributylamine.HBr complex, tributylamine.HI complex, tributylamine.tetrahaloboric acid complex, N,N'-dimethyl-1,2-diaminoethane.tetrahaloboric acid complex, and mixtures thereof and the like.

Other suitable catalysts include quaternary and tertiary ammonium, phosphonium, and arsonium adducts or complexes with suitable non-nucleophilic acids such as, for example, fluoboric, fluoarsenic, fluoantimonic, fluophosphoric, perchloric, perbromic, periodic, mixtures thereof and the like. U.S. Pat. No. 5,169,473 discloses latent catalysts that are useful for the present invention.

When applied and coated onto a substrate, separately or in a mixture, the ratios of curable resinous powder and superabsorbent polymeric powder may be present in a variety of amounts. Typically, the curable resinous powder is present in an amount from about 5 to about 20%, balance superabsorbent polymeric powder. It is preferred to utilize from about 5 to about 10% curable resinous powder, balance superabsorbent polymeric powder, to enhance liquid absorbance.

The powders and powder mixtures of the invention may be applied to a substrate with use of conventional means and techniques such as slot coating, Corona discharge guns, tribocharging apparatus, curtain coating, air-assisted coating techniques, etc.

Powders suitable for the invention may be made using conventional techniques such as extrusion and grinding. Conventional cryogenic grinding techniques may be desirable when grinding thermoplastic resinous material into powders due to the toughness of such material. It is also contemplated that superabsorbent polymers may be ground with the thermoplastic resin and the resultant product applied to a substrate in accordance with the invention. Typically, the respective materials may be in particulate form prior to grinding to obtain smaller particles. Production of very fine size distributions such as less than 10 microns, and even from 2 to 5 microns, can be manufactured with the use of jet milling or other technology. Direct particle production such as shown in U.S. Pat. Nos. 5,766,522; 5,708,039; 4,582,731; 4,734,451; 4,012,461; 5,027,742; 5,171,613; 4,734,227; 5,997,956; and 6,132,653 can also be used to produce particles for the invention. Said patents are incorporated herein by reference. It is also contemplated that directly produced particles or powders can be generated and then immediately placed in contact with the liquid coated polymeric material.

Above-mentioned U.S. Pat. No. 5,766,522 discloses the use of supercritical conditions to produce resinous particles. Carbon dioxide may be used as a solvent for the process. The Ohio State University College of Engineering, in its publication entitled, "News in Engineering," Vol. 70, No. 2, describes the treatment of polymers under supercritical conditions to expand polymer fibers to increase absorbency. This publication also discloses supercritical carbon dioxide can carry additives, such as molecules of surfactants or soaps, deep into materials such as cloth, plastic, and paper. However, there is no mention of carrying superabsorbent particles into such materials.

The process of the present invention permits incorporation of superabsorbent material (powder or film) into polymeric materials by treating the polymeric material with a superabsorbent material contained in supercritical fluid solvents, such as carbon dioxide, methanol, etc. Aforementioned U.S. Pat. No. 5,766,522 mentions various other suitable solvents.

It is contemplated by the present invention that resinous superabsorbent polymer particles or films could be generated in situ under supercritical conditions and then incorporated into a polymer that is being treated supercritical conditions, such as with supercritical carbon dioxide. Alternatively, pre-manufactured particles could be added under supercritical conditions to achieve incorporation. Under either process, liquid absorbency of the treated polymer would be increased, thereby offering a new class of highly absorbent products.

The invention may also be advantageously used to enhance the absorbency of cleaning products designed for wiping or absorbing liquids, particularly aqueous liquids, such as water or water-based liquids. Such products made according to the present invention exhibit increased rates of absorbency, especially during initial stages of use. Particle size distribution is important to achieve the rapid aqueous absorption rates required for wipes. To demonstrate this inventive characteristic, the absorbency data set forth below was obtained. Three different 0.1 gram powders, each having different particle size distributions, were placed in filter bags made from USA filter paper, which was made from non-chlorinated blended fibers and sold by Miniminit Products, Ltd., Scarborough, Ontario, Canada, and then immersed in a cup of distilled water for thirty seconds. The superabsorbent particles of Samples A and B were obtained from Aquatine, Inc., P.O. Box 5168, Lakeland, Fla. 33807, and sold under the name AOG-40 and AOG-44. Sample C was obtained by grinding and screening a portion of Sample B to a smaller size. The following experimental results were obtained and are set forth in the following table.

| Sample | SAP Particle Size Distribution | Weight Gain Including Filter Bag | Appearance of SAP Following Immersion |
|---|---|---|---|
| A (AOG-40) | 100% > 210 microns | 2.0 | Ball-like discreet particles contain absorbed water |
| B | 100% < 210 | 18.9 | Gel- or paste-like |

| Sample | SAP Particle Size Distribution | Weight Gain Including Filter Bag | Appearance of SAP Following Immersion |
|---|---|---|---|
| (AOG-44) | microns, 35% < 90 microns | | material containing absorbed water |
| C (AOG-44, ground and screened) | 100% < 90 microns | 19.7 | Gel- or paste-like material containing absorbed water |

Based upon the above data, it is clear that the gel- or paste-like resulting material exhibited much superior absorbance. Hence, a sufficiently small size distribution to achieve such gel-like material results in a superior wipe. Clearly, an SAP particle size distribution having a large proportion of particles less than 200 microns would achieve such gel and accompanying desired result. Sample C is consistent with the result of Sample B and achieves further superior absorbency.

As can be appreciated, the powder stably adhered to the cured resin coating should have a particle size distribution sufficient to form a gel upon contact with aqueous solutions. A convenient powder particle size distribution to form a gel is one having essentially about 100% of its particles below about 200 microns and 35% below about 100 microns. Finer particle size distributions, such as those having about 100% of its particles below about 100 microns, are believed to be further advantageous.

It should be understood that a wipe could comprise a polymeric material having a cured liquid resin and adhered superabsorbent powder on one or both wipe surfaces. Alternatively, an absorbent core of the above-coated material could be interposed between two water permeable sheets or between one water impermeable sheet and one water permeable sheet.

Two different SAP particle size distributions were evaluated to simulate conditions encountered during the use of a diaper. One-gram samples of each particle distribution were placed in the same filter papers described above. Samples and B correspond to Samples A and B of the above wiping experiments. The samples were immersed in a container having 0.9% wt % sodium chloride in water for five time intervals. This sodium chloride-containing solution was provided to simulate urine. the following experimental results were obtained and are set forth in the following table.

| Sample | SAP Particle Size Distribution | Weight Gain per one gram of Super Absorbent Polymer (in grams) after specified time (in minutes) | | | | |
|---|---|---|---|---|---|---|
| | | ½ min | 1 min | 5 min | 10 min | 30 min |
| A (AOG-40) | 100% > 210 microns | 7.1 | 11.58 | 19.52 | 27.60 | 33.85 |
| B (AOG-44) | 100% < 210 microns, 35% < 90 microns | 27.59 | 31.04 | 34.01 | 34.32 | 34.36 |

Based on the previously mentioned Atofina website, a typical diaper may contain anywhere about 10 grams to 20 grams of superabsorbent polymer. Normal diapers typically utilize about 10 grams or less of SAP and thinner diapers, pads, or adult incontinence products, contain from 10 to 20 grams of SAP. In general, the thinner the product, the higher amount of SAP that is included. Two diapers are weighed after usage, and the weight gain is approximately 200 grams. If 10 grams of SAP was used, then the weight gain per gram of SAP is about 20 grams. This indicates that normal usage time of a diaper corresponds to 5 and 10 minutes of the above experimental times. At 5 and 10 minutes, the difference in weight gain between respective particle sizes is very significant. The particles of Sample B can absorb about 75% more at 5 minutes and 25% more at 10 minutes. This indicates that the usage of SAP in diaper products may be reduced by at least 25% by weight, and similar performance with respect to the total absorbency of the diaper can be maintained. Another benefit is that the faster rate of absorption of the finer particles will maintain the contact surface drier than coarse particles.

The above data also indicate that thin absorbent products, such as adult incontinence products, can benefit to a greater extent regarding contained SAP weight than normal diapers because of the higher amount of the contained SAP. Another benefit is that such desirably thin products can be made even thinner without loss of important absorbency properties.

It is believed that the above Table indicates that finer particles lead to increased rates of absorbance, at least during initial usage times. Finer particles, at least during normal diaper usage times (prior to saturation) are believed to lead to increased total absorbance. Please note that the data following the 30 minutes of immersion is believed to reflect product saturation—an event that would rarely occur during actual use. It is believed that the data obtained following up to 10 minutes of immersion is more typical of actual use.

A general example of a typical combination of process steps that can produce the product of the invention is as follows:

First, a sheet of cellulosic fibers is provided and then is spray coated with a UV-curable liquid urethane resin. Then such coated fibrous material is contacted with superabsorbent polymeric powders comprised of sodium salts of polyacrylic acid having a size distribution wherein a large proportion of the particles are less than about 200 microns and thus is caused to adhere to the liquid resinous coating. This intermediate product is then exposed to ultraviolet radiation from H lamps with less than one second exposure to cure the resin and thereby stably affix or stably adhere the powder particles to the surface of the cured resin. The resultant sheet product is no longer tacky following the curing step and is then stacked with like sheets to form a liquid absorbent product or core which is then disposed between a liquid permeable sheet and a non-liquid permeable sheet to form a diaper.

Another process embodiment is illustrated below.

A sheet of cellulosic fibers is provided and then is coated with an aqueous solution containing a polyacrylic acid resin. Following evaporation of the water at a low temperature such as 100° F., the same powder described in the example is applied and the process is conducted in the same manner. A resultant product similar to that of the above example is obtained.

It will be understood that a coil of polymeric material, such as cellulosic material, could be used instead of an individual sheet and the process conducted in a continuous manner passing the coil web through various processing stations. The web can then be recoiled or individual sheets cut from the coil following the curing step. Also individual sheets can be placed in a moving belt and continuously or semi-continuously moved from a coating station to a powder application station, to a curing or melting station, and to a stacking station.

The data contained in the following table illustrates the use of thermoplastic resinous powders and superabsorbent polymeric powders for absorbent products.

| TRIAL | WT OF COTTON | WT OF SAP* | WT OF TRP** | TOTAL WEIGHT GAIN | THEORETICAL WEIGHT GAIN BY COTTON | WEIGHT GAIN BY SAP and TRP |
|---|---|---|---|---|---|---|
| A | 1.4 | — | — | 32.0 | — | — |
| B | 2.0 | 1.0 | — | 69.0 | 45.6 | 23.4 |
| C | 1.4 | — | 1.0 | 38.9 | 31.9 | 7.0 |
| D | 1.7 | 0.9 | 0.1 | 65.3 | 39.0 | 26.3 |
| E | 2.1 | 0.8 | 0.2 | 67.0 | 47.9 | 19.0 |
| F | 2.7 | 0.9 | 0.1 | 83.3 | 61.6 | 21.7 |

All weights in grams
*Superabsorbent polymeric powder
**Thermoplastic resinous powder The trials were conducted by immersing approximately 3-inch cotton squares containing the ingredient(s) specified in the above table into a 0.9 wt % NaCl aqueous solution for one minute. The cotton squares were separated into two essentially equal layers, the ingredient(s) were placed in between such layers, and the layers were lightly pressed together. The thermoplastic resinous material selected for the above trials is sold under the trademark EVAL® G156B by Eval Company of America, Pasadena, Tex. This resin is an ethylene vinyl alcohol copolymer containing 48 mol % ethylene. Following placement into the cotton square and prior to immersion, the samples containing the thermoplastic resinous powder were heated in a 200° C. oven for one minute. Such temperature and time was sufficient to melt the resin.

Example A indicates that the cotton fiber used in the trials absorbs about 22.8 grams of the aqueous solution per gram of cotton.

Example B indicates that one gram of fine superabsorbent polymeric powder (100%<210 microns, 35%<90 microns) absorbs about 23.4 grams of the aqueous solution.

Example C indicates that one gram of a fine thermoplastic resinous powder (<100 microns) absorbs about 7 grams of the aqueous solution.

Example D indicates that one gram of a mixture of a 10 wt % of fine thermoplastic resinous powder, balance fine superabsorbent polymeric powder, absorbs about 26.3 grams of the aqueous solution.

Example E indicates that one gram of a mixture of a 20 wt % of fine thermoplastic resinous powder, balance fine superabsorbent polymeric powder, absorbs about 19.0 grams of the aqueous solution.

Example F indicates that one gram of a mixture of a 10 wt % of coarse thermoplastic resinous powder, balance fine superabsorbent polymeric powder, absorbs about 21.8 grams of the aqueous solution.

Based upon the above information and observation the respective products following immersion, the following conclusions may be reached.

First, the thermoplastic resinous powder is effective in absorbing a minor, but significant, amount of the aqueous solution.

Second, all thermoplastic resinous powder containing samples exhibited a continuous gel-like appearance. Thus, ball-like products were prevented.

Third, lower wt percentages of thermoplastic resinous powder in the mixtures result in desirable gel-like products and lead to higher amounts of absorption.

Fourth, finer thermoplastic resinous powder particle size distributions should to lead to slightly higher amounts of absorption due to a larger surface area per unit of weight. However, coarser thermoplastic resinous powder particle size distributions are less costly to produce and could be preferred for cost reasons.

In summary, it is believed that fine superabsorbent polymeric powder may be adhered to fibrous substrates, such as cotton, without appreciable loss in absorbency. Thus, it is believed that the use of thermoplastic resinous powders to adhere fine superabsorbent polymeric powder to materials in absorbent products permits the improved absorbency benefit of the fine superabsorbent polymeric powder to be realized without incurring segregation of the particles in the absorbent product.

As mentioned previously, prior methods of erosion and irrigation control involve incorporating superabsorbent polymeric powder into soil to prevent erosion and water loss or placing elongated elements to form a barrier in soil to prevent erosion. The present invention utilizes superabsorbent polymeric powder in a distinct, highly advantageous manner to enhance erosion and irrigation control and to direct the growth of plant roots. Such advantages are obtained by stably adhering superabsorbent polymeric powder to elements designed to achieve various purposes.

Superabsorbent polymeric powder is stably adhered to water retention elements rather than being scattered or mixed into the soil. Such elements are stably adhered to superabsorbent polymeric powder, which absorb and store water under the ground. However, it is contemplated that superabsorbent polymeric powder may be distributed in the soil in combination with the use of the superabsorbent polymeric powder coated elements of the invention. Placement of these elements into the ground creates a stable system for absorbing and storing water introduced into the soil. Following storage, the absorbed water is then advantageously dispensed back into the ground and/or becomes absorbed by plant roots. The above-described invention avoids situations where the superabsorbent polymeric powder become washed away or segregated due to water introduction or other causes.

The elements may conveniently comprise rigid materials such as plastic, metal, wood, or other materials, or non-rigid woven or non-woven fibrous materials such as cotton, burlap, wood chips, plant husks, etc. The elements may preferably contain openings to permit the passage of water and nutrients. Such openings, in combination with the structure of the element, provide a free volume sufficient to permit the superabsorbent polymeric powder to expand upon contact with a liquid. Otherwise, water absorption could be retarded should an inadequate free volume exists. Honeycombed openings are contemplated as well as other types of openings. Suitable element shapes include sheets, cylinders, or other configurations. Cylindrical elements may be formed by wrapping a flat sheet into a cylinder. Multiple wrapped layers are contemplated. All elements may be coated on one or both sides. In the case of hollow or multiply wrapped cylindrical elements, the interior and/or exterior of such element may be coated; and sufficient free volume is created thereby. The element may be coated only on specific areas. In such case, an element could be inserted into the ground with only the coated area absorbing water. Such procedure would obviously enable water storage to be obtained at a specific location under the ground and not in an undesired area.

All of the methods previously described in this application for stably adhering superabsorbent polymeric powder to an element are suitable for use in preparing water retention elements for irrigation, erosion, and plant root direction usage.

Generally, copolymers of acrylic acid, acrylamide, and any bi-functional monomer that can provide cross-linking, are suitable for absorption/retention use. Anionic polyacrylamide polymers are an example of a suitable superabsorbent polymeric powder for water retention purposes.

Typical superabsorbent polymeric powder particle sizes for water retention applications may range from less than about 10 microns to about 5,000 microns or more. For example, a 500-1,000 micron particle size is suitable for most applications. Erosion control barrier elements, as well as water or petroleum elements, may benefit from smaller particle sizes because smaller particle sizes have the ability to absorb water and other liquids more quickly than larger particle sizes. The ability to rapidly absorb water is obviously beneficial to erosion control. In addition, rapid absorption of water and petroleum is obviously beneficial for clean-up applications. Particle sizes on the order of about 10 microns to about 100 microns are especially suitable for erosion control and clean up.

Typical amounts of superabsorbent polymeric powder that are scattered or mixed with soil are as follows: 50 gm/m$^2$ for grass irrigation; ½ kg/m$^3$ for tree, bush, or plant transplantation; and 100 gm/m$^2$ for surface application on growing plants. Similar quantities may be used in the practice of the present invention with exact quantities for all embodiments of the invention being within the skill of the art to determine for specific purposes, materials, climates, and soil conditions with the use of no more than routine experimentation.

Water retention elements may be generally placed under the ground by forming a hole in the ground, placing the element in the hole, and covering the hole. Alternatively, if the element has sufficient structural integrity and the ground is sufficiently soft, the element may be placed in a desired location by applying pressure to push the element into the ground. Such placement also provides aeration of the soil with accompanying root growth benefits. Mechanical devices may also be used to place the element at a desired location. For example, a sod-cutting machine could be used to lift sod from a lawn or athletic field, then a film or sheet-like element placed under the lifted sod, and the sod returned to its original location. If a roll or coil of elongated, cylindrical element were used, a machine similar to that used to lay cable in the ground could be employed. Such machine digs a trench, uncoils the cable into the trench, and then covers the trench. It is also contemplated that elements could be placed in the ground during plowing with use of a coil element that is continuously fed into the furrow created during plowing.

Superabsorbent polymeric powder-coated elements may be placed in the ground to prepare for future usage or placed in the ground after the usage has commenced. For example, a grid of superabsorbent polymeric powder-coated elements may be placed at an underground location an then an athletic field, golf course fairway or green, lawn, crop, plant, etc. then placed or grown over such grid. Different elements may be placed at different depths in the ground to provide water and nutritional assistance as growth progresses. Alternatively, the elements can be placed underground following the commencement of growth on top of the ground. The ability to place coated elements in the ground following establishment of a plant or crop is important because the above-described prior art technique of placing absorbent particles below the ground would become difficult, if not impossible.

As mentioned previously, loose absorbent particles have been used to clean up liquids, including standing water and petroleum spills. Once the particle has absorbed the liquid, the particle itself must be collected to complete the clean-up operation. Collection may be a tedious process. The present invention provides a solution to the above-described clean-up problem. The invention may be used to collect standing water caused by rain from the surface of athletic fields or golf courses, including greens. The collection or clean up of petroleum spills on land or water is also contemplated. By stably adhering an appropriate absorbent polymer on a clean-up element such as a porous sheet, and then placing such sheet in contact with the liquid, one can easily absorb the liquid and then remove the sheet, thereby avoiding the need for tedious particle collection and removal. The previously mentioned superabsorbent polymeric powders are suitable for water clean up, and various well-known petroleum absorbent polymeric powders can be used for petroleum clean up. Such polymers include PETRO BOND® sold by Nochar and PETROLSORB® sold by Polymers, Inc.

Examples of irrigation and erosion control systems of the present invention are set forth below.

EXAMPLE G

Erosion control is affected by placing flat, elongated polymeric barrier elements having openings and coated with stably adhered superabsorbent polymeric powder into a steep bank where soil erosion is desired to be prevented. For example, hills, terraces, stream banks, or other areas where erosion is undesirable, could benefit from this procedure. The barrier element absorbs water rapidly and then holds such absorbed water until a time when the water is gradually released from the superabsorbent polymeric powder back into the soil. Such cycle is repeated as the relative amount of water in the soil changes.

EXAMPLE H

Example G is repeated except that cylindrical erosion barrier elements are employed. Such barriers are coated on interior surfaces with superabsorbent polymeric powder. Holes are made in the soil, cylindrical erosion barrier elements are placed in such holes, and the hold is covered with soil to permanently affix the erosion barrier in the hole.

EXAMPLE I

Example H is repeated except that the cylindrical erosion barrier element has a pointed end and is placed into the soil by applying sufficient pressure to the other end of the cylinder to cause the cylinder to penetrate and become lodged in the soil. Alternatively, the element is in the form of a spiral and is screwed into a desired site in the soil.

EXAMPLE J

A lawn is desired to be irrigated by spraying water on the surface of the lawn. Prior to irrigation, a flat element coated with stably adhered superabsorbent polymeric powder is placed beneath and parallel to the surface of the lawn. Upon watering the lawn, water passes through the surface of the lawn into the underlying soil and is absorbed and retained by the element. The absorbed water is released when the soil becomes dry again and is utilized to feed the lawn, thereby reducing the need for future watering.

EXAMPLE K

Example J is repeated except that in addition to the above-described placement of the flat element, other elements are placed perpendicular to the surface of the lawn and along the lawn perimeter and retain water that would otherwise escape from the perimeter of the lawn.

EXAMPLE L

Examples J and K are repeated except that the lawn is located on an athletic field.

EXAMPLE M

Example J is repeated and the flat element is placed under the lawn by lifting the lawn sod and inserting the flat element thereunder.

EXAMPLE N

Example J is repeated and the element is cylindrical and is placed under the lawn by using an apparatus capable of digging a trench in the lawn, placing the, cylindrical element in such trench, and then replacing the sod removed by such digging onto the top of the trench, thereby burying the cylindrical element.

EXAMPLE O

A nursery desires to grow young trees and then transplant such trees to another area for subsequent growth. A common problem with the above procedure is that the roots from the young trees extend beyond the area where the root-containing ball of the tree is dug out. The roots extending beyond the ball area must be severed during removal. Removal of such roots adversely impacts subsequent tree growth. The following procedure is used to prevent the above problem. When growth of the young trees is initiated, water retention elements are placed in the contemplated root ball area. Upon watering the trees, the elements absorb and retain water, thereby causing the root system of the young tree to become focused in the area of the elements and extend into a non-desired area located away from the contemplated root ball area to a lesser extent than had the elements not been placed as described above. The trees become more mature and are then removed, stored, and transplanted to a new location.

EXAMPLE P

A homeowner is experiencing underground sewer clogging and damage because of tree roots entering into the sewer seeking water. Water retention elements are placed at location(s) sufficiently remote from the sewer to attract the tree roots, and the sewer is cleaned. Future clogging and damage to the sewer is minimized thereby.

EXAMPLE Q

A homeowner is experiencing damage to a driveway because tree roots are causing breakage of the driveway. Water retention elements are placed at several locations sufficiently remote from the driveway to attract the tree roots, thereby preventing further damage to the driveway.

EXAMPLE R

It is desired to grow a tree having a deep root system in an arid area. Normally, it is very difficult to grow such a tree because water is not available at a deep location to attract the roots. Consequently, if the tree can be grown at all, a shallow root system will develop; and the tree will be vulnerable to uprooting due to wind, etc. To prevent such problem, a water retention element is placed under a deep rooting tree at a location where roots are attracted. Water is absorbed and obtained by the water retention element and becomes dispersed into the soil as the soil becomes drier. Deep roots are formed.

EXAMPLE S

It is desired to cause seedling tree roots to grow in a desired location. Prior to planting the seed, water retention elements are placed in the ground at a location defining the volume of ground that will be utilized as a ball for subsequent tree transplantation. A seed is planted in the ground and grows into a seedling tree. The roots of the seedling tree are attracted to the water retention elements and are substantially directed to the above-mentioned ball location. The tree is removed along with the ball from the ground and transplanted to another location.

EXAMPLE T

Example S is repeated except that the water retention elements are placed at desired locations after the seedling tree has begun to grow.

EXAMPLE U

A person desires to go on an extended vacation and is unable to locate a service to ensure that the potted plants will be watered during the vacation. Water retention elements are placed in the soil surrounding the plant roots. The water retention elements are hollow, cylindrical elements coated on the inside of the cylinder with superabsorbent polymeric powder. The hollow nature of the cylinder permits the requisite free volume. The elements are placed in the soil by applying pressure to one end of the cylinder causing the element to enter the soil and become located at a desired location. A large amount of water is then introduced to the soil. Some of the provided water is utilized by the plant, and other portions of the water are absorbed by the superabsorbent polymeric powder and thus become stored at a desired location. In the absence of the water retention elements, a large portion of the provided water would have passed through the soil and out of the pot through a hole at its bottom. While the person is on vacation, the stored water is dispensed from the superabsorbent polymeric powder into the soil as the soil becomes dry and is utilized to water the plant roots. Thus, the need for plant watering while the person is on vacation is eliminated.

EXAMPLE V

Rain causes standing water to accumulate on a green during a golf tournament, thus causing a delay in play after the rain stops. Workers place a polymeric screen having superabsorbent polymeric powder stably adhered to the screen into the standing water area of the green. Water is absorbed by the powder, and water is removed from the surface of the green. Multiple placements of additional coated screens are performed until a sufficient amount of the standing water has been removed to permit play to continue.

EXAMPLE W

A petroleum spill occurs on a small body of water. Workers travel to the area of the spill and place a flat clean-up element comprising a polymeric screen stably adhered to a petroleum absorbent polymeric powder into the area of the spill. Petroleum is absorbed by the powder, and the element is removed thereby cleaning up at least a portion of the spilled petroleum.

EXAMPLE X

Example W is repeated, except that the petroleum spill occurs on land, and the clean-up element is unwrapped from a coil, passed continuously through the petroleum spill area, and then recoiled.

We claim:

1. An underground water retention element for collecting, storing, and dispensing water into soil at an underground location comprising a hollow generally cylindrical substrate located in soil at an underground location; said substrate having particles of a superabsorbent polymeric powder stably adhered thereto by a resinous material; said substrate having a structure including openings extending through said substrate which, in combination with the hollow nature of said substrate, is sufficient to permit passage of water through said openings and sufficient to create adequate free volume to permit said stably adhered superabsorbent polymeric powder to expand upon contact with water and to collect, store, and dispense water into said soil.

2. The water retention element of claim 1, wherein said superabsorbent polymeric powder comprises an anionic polyacrylamide polymer.

3. The water retention element of claim 1, wherein said superabsorbent polymeric powder comprises carboxymethyl starch.

4. The water retention element of claim 1, wherein said superabsorbent polymeric powder comprises acrylic grafted starch.

5. The water retention element of claim 1, wherein said water retention element comprises an elongated erosion barrier.

6. The water retention element of claim 1, wherein said water retention element is coated with said superabsorbent polymeric powder, said resinous material, and a plant nutrient.

7. The water retention element of claim 1, wherein said resinous material comprises a thermoplastic resinous coating powder.

8. The water retention element of claim 1, wherein said resinous material comprises a film of thermoplastic material.

9. The water retention element of claim 1, wherein said resinous material comprises a cured thermosetting coating powder.

10. The water retention element of claim 1, wherein said resinous material comprises a cured liquid resin.

11. An underground water retention element for collecting, storing, and dispensing water into soil at an underground location comprising a rigid, hollow generally cylindrical substrate located in soil at an underground location; said rigid substrate having particles of a superabsorbent polymeric powder stably adhered thereto by a resinous material; said rigid substrate having a structure including openings extending through said substrate which, in combination with the hollow nature of said substrate, is sufficient to permit passage of water through said openings and sufficient to create adequate free volume to permit said stably adhered superabsorbent polymeric powder to expand upon contact with water and to collect, store, and dispense water into said soil.

12. The water retention element of claim 11, wherein said openings are honeycombed.

13. The water retention element of claim 11 wherein said cylinder comprises a sheet wrapped to form a cylinder.

14. The water retention element of claim 11 wherein said cylinder is coated with said superabsorbent polymeric powder and said resinous material on an interior portion of said hollow cylinder.

15. The water retention element of claim 11 wherein said water retention element comprises an elongated erosion barrier.

16. The water retention element of claim 11, wherein said water retention element is coated with said superabsorbent polymeric powder, said resinous material, and a plant nutrient.

17. The water retention element of claim 11 wherein said resinous material comprises a thermoplastic resinous coating powder.

18. The water retention element of claim 11 wherein said resinous material comprises a film of thermoplastic material.

19. The water retention element of claim 11 wherein said resinous material comprises a cured thermosetting coating powder.

20. The water retention element of claim 11 wherein said resinous material comprises a cured liquid resin.

21. The water retention element of claim 11 wherein said superabsorbent polymeric powder comprises an anionic polyacrylamide polymer.

22. The water retention element of claim 11, wherein said rigid hollow generally cylindrical substrate has a pointed end.

23. The water retention element of claim 11, wherein said rigid hollow generally cylindrical substrate is in the form of a spiral.

24. The water retention element of claim 1, wherein said cylinder comprises multiple wrapped layers.

25. The water retention element of claim 11, wherein said cylinder comprises multiple wrapped layers.

* * * * *